United States Patent
Chen

(10) Patent No.: US 9,089,546 B2
(45) Date of Patent: Jul. 28, 2015

(54) SYNERGISTIC COMPOSITIONS CONSISTING ESSENTIALLY OF COMBINATIONS OF ACTIVE AGENTS SELECTED FROM ORIDONIN, WOGONIN, AND ISOLIQUIRITIGENIN FOR THE PREVENTION OF NEOPLASIA

(75) Inventor: Sophie Chen, London (GB)

(73) Assignee: ACTIVEPHYTO TECHNOLOGIES LIMITED, Jersey (GB)

( * ) Notice: Subject to any disclaimer, the term of this patent is extended or adjusted under 35 U.S.C. 154(b) by 1413 days.

(21) Appl. No.: 12/300,350

(22) PCT Filed: May 10, 2007

(86) PCT No.: PCT/GB2007/001720
§ 371 (c)(1),
(2), (4) Date: Apr. 6, 2009

(87) PCT Pub. No.: WO2007/132190
PCT Pub. Date: Nov. 22, 2007

(65) Prior Publication Data
US 2010/0016420 A1    Jan. 21, 2010

(30) Foreign Application Priority Data
May 11, 2006 (GB) .................................. 0609386.8

(51) Int. Cl.
| | |
|---|---|
| *A61K 31/352* | (2006.01) |
| *A61K 45/06* | (2006.01) |
| *A61K 31/121* | (2006.01) |
| *A61K 31/353* | (2006.01) |

(52) U.S. Cl.
CPC .............. *A61K 31/352* (2013.01); *A61K 31/121* (2013.01); *A61K 31/353* (2013.01); *A61K 45/06* (2013.01)

(58) Field of Classification Search
CPC .. A61K 31/352; A61K 45/06; A61K 2300/00
See application file for complete search history.

(56) References Cited

U.S. PATENT DOCUMENTS

2003/0035851 A1   2/2003  Chen
2005/0032882 A1*  2/2005  Chen ............................. 514/456

FOREIGN PATENT DOCUMENTS

| GB | 1 476 016 A | 6/1977 |
| WO | WO 2004/080474 A | 9/2004 |

OTHER PUBLICATIONS

Chen, S., et al., "Combined Activity of Oridonin and Wogonin in Advanced-Stage Ovarian Cancer Cells," *Cell Biol. Toxicol.*, 27:133-147 (2011).

* cited by examiner

*Primary Examiner* — Samira Jean-Louis
(74) *Attorney, Agent, or Firm* — Antoinette G. Giugliano; AGG Intellectual Property Law

(57) ABSTRACT

The present invention relates to the treatment of therapy-resistant neoplasias. The compounds and methods of the invention are particularly useful for the treatment of taxol-resistant human cancers, particularly cervical and breast cancer. Components of the compositions of the present invention show strong synergy with one another allowing them to be used in relatively low amounts for the treatment of stage IV or recurrent cancer which may have grown resistant to the traditional chemotherapeutic agents. These compositions comprise oridonin.

9 Claims, No Drawings

SYNERGISTIC COMPOSITIONS CONSISTING ESSENTIALLY OF COMBINATIONS OF ACTIVE AGENTS SELECTED FROM ORIDONIN, WOGONIN, AND ISOLIQUIRITIGENIN FOR THE PREVENTION OF NEOPLASIA

RELATED APPLICATIONS

This application is the U.S. National Phase of International Application No. PCT/GB2007/001720, filed 10 May 2007, published in English, which application claims priority under 35 U.S.C. §119 or 365 to Great Britain Application No. 0609386.8, filed 11 May 2006. The entire teachings of the above applications are incorporated herein by reference.

FIELD OF THE INVENTION

The present invention relates to the treatment of therapy-resistant neoplasias. Particularly, although not exclusively, the present invention relates to a combination of active agents and a method useful in the treatment of taxol-resistant human cancers.

BACKGROUND

Cancer is a leading cause of suffering and death throughout the world and is expected to increase in prevalence as modern technologies extend life expectancy. Occasionally over the lifetime of a cell there are slight alternations made to the DNA known as mutations. Some of these mutations, known as 'silent mutations', do not result in any physical changes to the function of the cells but others can change the way a cell behaves.

A number of mechanisms exist to prevent a cell in which a mutation has occurred from proceeding in the cell cycle, and if the genetic error is not corrected, the cell will "commit suicide" in a process known as apoptosis. However, if a mutation occurs in a protein involved in cell cycle regulation, this can lead to uncontrolled proliferation of cells, known as neoplasia, which in turn may progress to cancer.

Cancer cells typically have an adverse effect on the body. The cancer can spread by invasion of adjacent tissues by malignant neoplastic tumor cells, and by a process known as metastasis, where the malignant cells dissociate from the tumour mass and spread to distant sites. Cancer manifests itself in a wide variety of forms, in many different types of tissue and is can be characterised by its degree of invasiveness and aggressiveness.

Cancer may be treated in a number of ways including surgery, radiation therapy and chemotherapy. The exact type of therapy used may depend on one or more of a number of factors, such as, what stage the cancer has reached, whether and where it has spread to and what the likely effects on lifestyle may be.

Various treatment methods may be used in concert to achieve improved therapy. For example, a tumour may be surgically removed and chemotherapy or radiation therapy then used to target remaining cancer cells. However, the various methods may be used alone with good results.

Chemotherapy involves the administration of drugs often targeted to rapidly dividing cells. Many chemotherapeutic drugs interfere with DNA replication prior to cell division. Although there have been many advances in chemotherapeutic agents, the genetic instability of cancer cells, especially advanced cancers, leads to a high incidence of drug resistant cancers and even multi-drug resistance (MDR).

Two favoured chemotherapeutic agents, taxol and cisplatin are used in combination to treat stage IV, the most advanced stage, and recurrent disease. As would be appreciated, failure to respond to either of these agents, or indeed the combination of both, leaves oncologists with limited therapeutic options going forward.

It would be useful if a therapeutic agent or combination of agents were available to treat therapy resistant cancers.

It is therefore an object of the present invention to provide agents useful in the treatment of therapy-resistant cancers.

SUMMARY OF THE INVENTION

In a first aspect the present invention provides the use of a compound having the structure of Formula I;

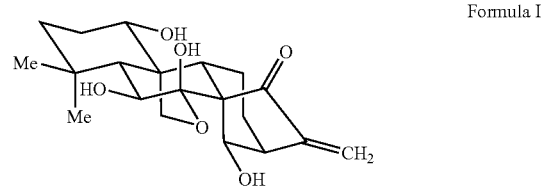 [SMILES: C=C1C(=O)C23C(O)C1CCC2C12COC3(O)C(O)C1C(C)(C)CCC2O]

Formula I its pharmaceutically acceptable salts and esters, selectively substituted analogues, or a combination of one or more of the foregoing compounds and one or more of;

a compound having the structure of Formula II.

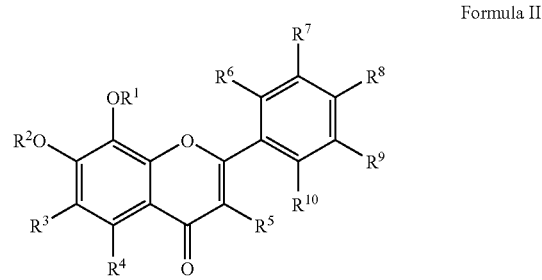

Formula II wherein $R^1$ is hydrogen, $C_1$-$C_6$ alkyl; $R^2$ is hydrogen, $C_1$-$C_6$ alkyl, or $C_2$-$C_6$ acyl; and $R^3$-$R^{10}$ are independently hydrogen, hydroxy, $C_1$-$C_6$ alkyl, $C_1$-$C_6$ alkoxy, or $C_2$-$C_6$ acyl, with the proviso that at least four of $R^3$-$R^{10}$ are hydrogen, its pharmaceutically acceptable salts and esters, selectively substituted analogues, or a combination of one or more of the foregoing compounds; and a compound having the structure of Formula IV

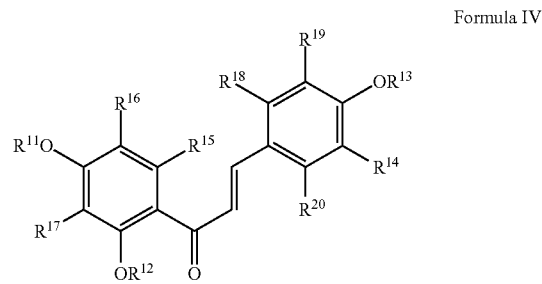

Formula IV wherein $R^{11}$-$R^{13}$ are independently hydrogen or $C_1$-$C_6$ alkyl; and $R^{14}$-$R^{20}$ are independently hydrogen, $C_1$-$C_6$ alkyl, $C_1$-$C_6$ alkoxy, or $C_2$-$C_6$ acyl, with the proviso that at least three of $R^{14}$-$R^{20}$ are hydrogen, its pharmaceutically acceptable salts and esters, selectively substituted analogues, or a combination of one or more of the foregoing compounds The neoplasia to be treated may be malignant or benign and in preferred embodiments may be selected from the group of hormone-dependent cancers. Specifically, the preferred neoplasia to be treated with the medicaments according to the present invention may be any one or more neoplasia selected from the group consisting of prostate cancer, breast cancer, endometrial cancer, colon cancer, lung cancer, bladder cancer, testicular cancer, ovarian cancer, thyroid cancer or bone cancer. Preferably the neoplasia to be treated are human cancers.

In one particularly preferred embodiment the medicaments of the invention may be used to treat taxol-resistant ovarian or breast cancer.

The compound having the structure of Formula II is preferably substituted so that $R^1$ is methyl, $R^2$ is hydrogen, and $R^3$-$R^{10}$ are independently hydrogen, methyl, ethyl, methoxy, ethoxy, acetyl, or propionyl, with the proviso that at least five of $R^3$-$R^{10}$ are hydrogen.

The compound having the structure of formula II is most preferably substituted so that it has the structure of Formula III.

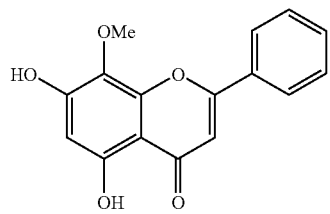

Formula III

The compound having the structure of Formula IV is preferably substituted so that $R^{11}$-$R^{13}$ are hydrogen and $R^{14}$-$R^{20}$ are independently hydrogen, methyl, ethyl, methoxy, ethoxy, acetyl, or propionyl, with the proviso that at least four of $R^{14}$-$R^{20}$ are hydrogen.

The compound having the structure of formula IV is most preferably substituted so that it has the structure of Formula V.

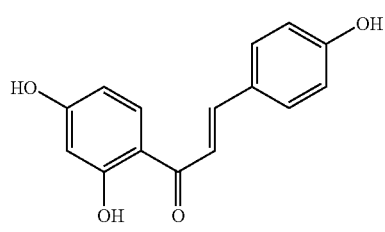

Formula V

The resistant cancers treated with the medicaments according to the present invention may be taxol-resistant or cisplatin-resistant cancers.

In preferred embodiments the resistant cancers to be treated with the medicaments of the invention are taxol-resistant cancers.

The present invention also provides a composition for the treatment of a drug-resistant cancer comprising a pharmaceutically effective amount of a compound according to Formula I, its pharmaceutically acceptable salts and esters, selectively substituted analogues, or a combination of one or more of the foregoing compounds and one or more of;
    a compound of Formula II, its pharmaceutically acceptable salts and esters, selectively substituted analogues, or a combination of one or more of the foregoing compounds; and
    a compound of Formula IV, its pharmaceutically acceptable salts and esters, selectively substituted analogues, or a combination of one or more of the foregoing compounds.

Preferably the composition contains a compound of Formula III.

Preferably the composition contains a compound of Formula V.

In preferred embodiments the compositions according to the present invention may additionally comprise both a compound of Formula II and a compound of Formula IV, their pharmaceutically acceptable salts and esters, their selectively substituted analogues, or a combination of two or more of the foregoing compounds.

The medicaments of the invention may comprise compounds having Formula III and Formula V.

The medicaments of the invention may additionally comprise any number of additional chemotherapeutic agents or agents which may be co-administered with chemotherapeutic agents in order to enhance their effect, for example growth factors such as TNFα, caspase inhibitors or any other agent that may enhance the therapeutic effect to be obtained from the inventive medicament.

The medicaments of the invention may take the form of a tablet, capsule, indictable solution, implantable slow release matrix or device or any other form known in the art.

The compounds for use as active agents in the medicaments according to the present invention may be derivatized to provide for, for example, site-directed application, resistance to gastrointestinal breakdown, and/or to improve pharmaco-kinetic properties.

The medicaments according to the invention may also take the form of a powder for direct inhalation, a suppository, or a solution which may be suitable for transdermal application. For example, one medicament according to the invention may simple comprise a solution of the active agent (S) in dimethyl sulphoxide.

The medicaments according to the invention may be manufactured using any methods known in the art. For example, the compositions may be dry milled and mixed prior to tableting and the composition may therefore necessarily contain other pharmaceutically expectable excipients such as a lubricant selected from the group consisting of calcium stearate, magnesium stearate, zinc stearate, stearic acid, talc and combinations thereof, a binding agent selected from the group consisting of hydroxypropylmethyl cellulose, hydroxyethyl cellulose, hydroxypropyl cellulose, methyl cellulose and a polyvinyl pyrrolidone (PVP).

Medicaments according to the invention may contain any pharmaceutically acceptable excipients such as binders, fillers, pigments, disintegrating agents, lubricants, wetting agents, buffers and other excipients conventionally used in the pharmaceutical and chemical fields. Some examples of excipients for use in the medicaments of the present invention are microcrystalline cellulose, lactose, starch, colloidal silica, talc, glycerol esters, sodium stearyl fumarate, and titanium dioxide.

Methods

In a further aspect the present invention also provides a method of treating a human in need of therapy resistant neoplasia treatment, comprising administering a composition comprising greater than or equal to about 0.5% w/w of a compound having the structure of Formula I;

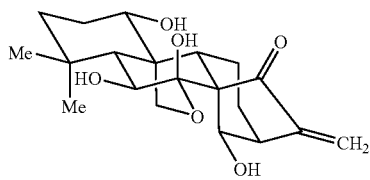

Formula I its pharmaceutically acceptable salts and esters, selectively substituted analogues, or a combination of one or more of the foregoing compounds, and one or more of;
a compound having the structure of Formula II.

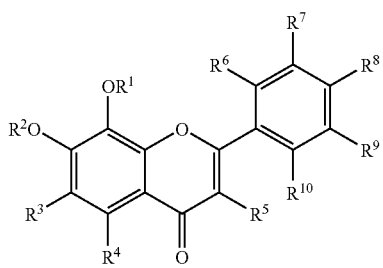

Formula II wherein $R^1$ is hydrogen, $C_1$-$C_6$ alkyl; $R^2$ is hydrogen, $C_1$-$C_6$ alkyl, or $C_2$-$C_6$ acyl; and $R^3$-$R^{10}$ are independently hydrogen, hydroxy, $C_1$-$C_6$ alkyl, $C_1$-$C_6$ alkoxy, or $C_2$-$C_6$ acyl, with the proviso that at least four of $R^3$-$R^{10}$ are hydrogen, its pharmaceutically acceptable salts and esters, selectively substituted analogues, or a combination of one or more of the foregoing compounds; and
a compound having the structure of Formuls IV

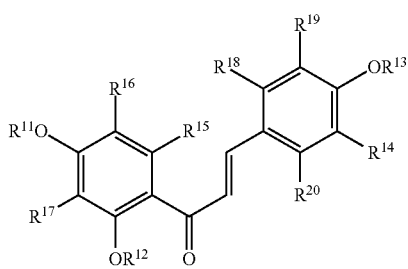

Formula IV wherein $R^{11}$-$R^{13}$ are independently hydrogen or $C_1$-$C_6$ alkyl; and $R^{14}$-$R^{20}$ are independently hydrogen, $C_1$-$C_6$ alkyl, $C_1$-$C_6$ alkoxy, or $C_2$-$C_6$ acyl, with the proviso that at least three of $R^{14}$-$R^{20}$ are hydrogen, its pharmaceutically acceptable salts and esters, selectively substituted analogues, or a combination of one or more of the foregoing compounds.

The neoplasia to be treated by the method of the invention may be malignant or benign and in preferred embodiments may be selected from the group of hormone-dependent cancers. Specifically, the preferred neoplasia to be treated with the method according to the present invention may be any one or more neoplasia selected from the group consisting of prostate cancer, breast cancer, endometrial cancer, colon cancer, lung cancer, bladder cancer, testicular cancer, ovarian cancer, thyroid cancer or bone cancer. Preferably the neoplasia to be treated are human cancers.

In one particularly preferred embodiment the method of the invention may be used to treat taxol-resistant ovarian and breast cancer.

The compound having the structure of Formula II is preferably substituted so that $R^1$ is methyl, $R^2$ is hydrogen, and $R^3$-$R^{10}$ are independently hydrogen, methyl, ethyl, methoxy, ethoxy, acetyl, or propionyl, with the proviso that at least five of $R^3$-$R^{10}$ are hydrogen.

The compound having the structure of formula II is most preferably substituted so that it has the structure of Formula III.

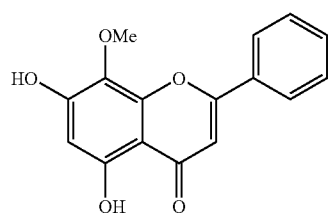

Formula III

The compound having the structure of Formula IV is preferably substituted so that $R^{11}$-$R^{13}$ are hydrogen and $R^{14}$-$R^{20}$ are independently hydrogen, methyl, ethyl, methoxy, ethoxy, acetyl, or propionyl, with the proviso that at least four of $R^{14}$-$R^{20}$ are hydrogen.

The compound having the structure of formula IV is most preferably substituted so that it has the structure of Formula V.

Formula V

The therapy resistant neoplasia to be treated with the method according to the present invention may be taxol-resistant or cisplatin-resistant cancers. In particularly preferred embodiments the method of the invention may be used to treat taxol-resistant ovarian cancer.

The method of the present invention preferably involves the administration of compounds according to Formulae I, II and V.

Compositions

The present invention also provides a composition comprising greater than or equal to about 0.5% w/w based on the total weight of the composition of a compound having the structure of Formula I;

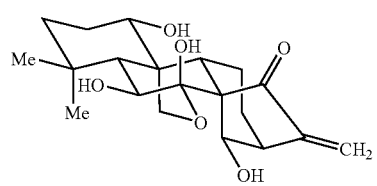

Formula I its pharmaceutically acceptable salts and esters, selectively substituted analogues, or a combination of one or more of the foregoing compounds, and one or more of; greater than or equal to about 0.5% w/w based on the total weight of the composition of a compound having the structure of Formula II.

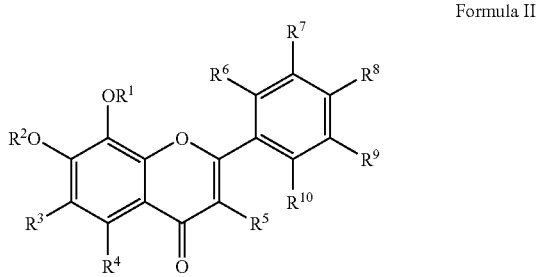

Formula II wherein $R^1$ is hydrogen, $C_1$-$C_6$ alkyl; $R^2$ is hydrogen, $C_1$-$C_6$ alkyl, or $C_2$-$C_6$ acyl; and $R^3$-$R^{10}$ are independently hydrogen, hydroxy, $C_1$-$C_6$ alkyl, $C_1$-$C_6$ alkoxy, or $C_2$-$C_6$ acyl, with the proviso that at least four of $R^3$-$R^{10}$ are hydrogen, its pharmaceutically acceptable salts and esters, selectively substituted analogues, or a combination of one or more of the foregoing compounds; and greater than or equal to about 0.5% w/w based on the total weight of the composition of a compound having the structure of Formula IV

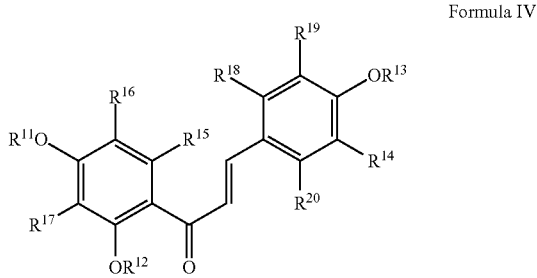

Formula IV wherein $R^{11}$-$R^{13}$ are independently hydrogen or $C_1$-$C_6$ alkyl; and $R^{14}$-$R^{20}$ are independently hydrogen, $C_1$-$C_6$ alkyl, $C_1$-$C_6$ alkoxy, or $C_2$-$C_6$ acyl, with the proviso that at least three of $R^{14}$-$R^{20}$ are hydrogen, its pharmaceutically acceptable salts and esters, selectively substituted analogues, or a combination of one or more of the foregoing compounds.

The compound having the structure of Formula II is preferably substituted so that $R^1$ is methyl, $R^2$ is hydrogen, and $R^3$-$R^{10}$ are independently hydrogen, methyl, ethyl, methoxy, ethoxy, acetyl, or propionyl, with the proviso that at least five of $R^3$-$R^{10}$ are hydrogen.

The compound having the structure of formula II is most preferably substituted so that it has the structure of Formula III.

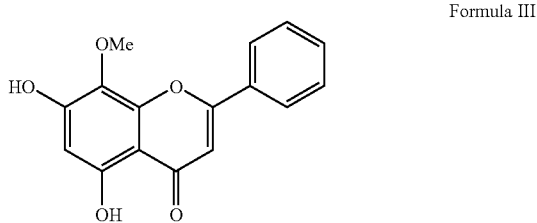 [SMILES: COc1c(O)cc(O)c2c(=O)cc(-c3ccccc3)oc12]

Formula III

The compound having the structure of Formula IV is preferably substituted so that $R^{11}$-$R^{13}$ are hydrogen and $R^{14}$-$R^{20}$ are independently hydrogen, methyl, ethyl, methoxy, ethoxy, acetyl, or propionyl, with the proviso that at least four of $R^{14}$-$R^{20}$ are hydrogen.

The compound having the structure of formula IV is most preferably substituted so that it has the structure of Formula V.

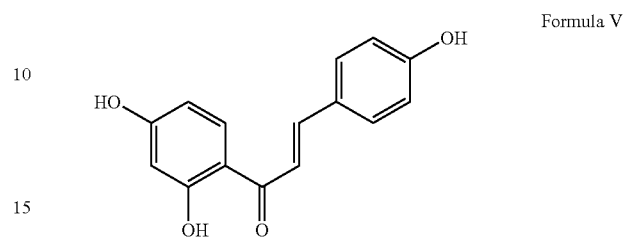

Formula V

The compositions of the present invention may have advantageously been used for treating hormone-dependent cancers. Specifically, the cancers to be treated with the medicaments and compositions according to the present invention may be selected from a prostate cancer, breast cancer, endometrial cancer, colon cancer, lung cancer, bladder cancer, testicular cancer, ovarian cancer, thyroid cancer or bone cancer.

The compositions of the present invention preferably contain the compounds according to Formulae I, III and V.

In the use, method and compositions of the present invention the compounds are preferably present in synergistically effective amounts. In those binary combinations the two ingredients are present in synergistically effective amounts with respect to one another. In those combinations of three or more active agents, the active agents may be present in synergistically effective amounts with respect to each other and/or the composition may be synergistic as a whole.

The compositions and medicaments of the invention may additionally comprise known anti-cancer agents and immune stimulants. Preferably the anti-cancer agents for use in the method, compositions and medicaments of the invention may be selected from indirubin, taxol, cis-platin, camptothecan, vincristine, monocrotaline, Maytansine, homoharringtonine, colchicine, irisquinone A, irisquinone B, irisquinone C, cronycine, matrin, oxymatrin, curcumin, paricine, pariphyllin, or a combination comprising one or more of these and other known anti-cancer agents.

Preferably the immune stimulant for use in the method, compositions and medicaments of the invention may be selected from a ginsenoside, ferulic acid, mannan, synanthrin, eleutheroside A, eleutheroside B, eleutheroside C, eleutheroside D, eleutheroside E, gynoside, beta-pachyman, inulin, glycoproteins, interferones, γ-globulins, an extract of *Ganoderma lucidum*, an extract of *Coriolus versicolor*, an extract of *Poria cocos*, or a combination comprising one or more of these and other known immune stimulants For oral administration compositions or medicaments of the invention may be administered with any inert diluent or with an edible carrier. They may be incorporated directly into food or beverages making up part of the patient's diet. The compositions or medicaments of the invention may be formulated with excipients and used in the form of ingestible tablets, buccal tablets, troches, capsules, elixirs, suspension syrups, wafers, and the like.

The tablets, troches, pills, capsules and the like may contain those excipients already mentioned and in some cases may also contain sweetening agents, such as sucrose, glucose, aspartame or saccharin, flavouring agents such as essential oils of mint, peppermint, spearmint or any other suitable flavouring. When the dosage unit is a capsule it may additionally contain a liquid carrier such as an oil or buffered aqueous solution.

Medicaments and compositions of the invention may also be formulated with phospholipids or fatty acids or other synthetic nanoparticles as carriers.

Medicaments and compositions of the invention may take the form of formulations for parenteral administration and may include sterile aqueous solutions or dispersions, and sterile powders for the preparation of sterile, injectable solutions or dispersions. The solutions or dispersions may also contain buffers, diluents, and other suitable additives that may be designed to promote the cellular uptake of the active agents in the composition, for example, liposomes.

Pharmaceutical formulations for topical administration may be especially useful for localized treatment. Formulations for topical treatment included ointments, sprays, gels, suspensions, lotions, creams, and the like. Formulations for topical administration may include known carrier materials such as isopropanol, glycerol, paraffin, stearyl alcohol, polyethylene glycol, and the like. The pharmaceutically acceptable carrier may also include a known chemical absorption promoter or the formulation may be specifically designed to facilitate transdermal application. Absorption promoters include, for example, trichloroethanol, trifluoroethanol, and certain alcohols and mixtures thereof according to GB 1,001, 949 to Meyer and GB 1,464,975 to AstraLakemedel).

Medicaments and compositions of the invention suitable for rectal or vaginal administration may be presented as a suppository, which may include one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Disclosed herein are medicaments, compositions and methods for treating neoplasia and cancer in a human in need of such treatment. As used herein, a human in need of treatment may be a patient diagnosed with cancer, or a patient wanting to prevent or delay the onset of cancer, for example, someone with a family history of cancer. The cancer may be a hormone-related cancer such as, for example, prostate cancer, breast cancer, endometrial cancer, colon cancer, lung cancer, bladder cancer, testicular cancer, ovarian cancer, thyroid cancer, or bone cancer.

In one particularly preferred embodiment the neoplasia to be treated may be taxol-resistant ovarian or breast cancer.

When esterified, the ester of the compound of Formula IV or V is preferably a glycoside. There is no particular limit on the monosaccharide or polysaccharide used to form the glycoside and suitable monosaccharides include, for example, glucose, glucuronic acid, mannose, fructose, galactose, arabinose, galacturonic acid, xylose, rutinose, rhamnose, and the like, and combinations comprising one or more of the foregoing monosaccharides. Suitable polysaccharides include, for example, dimers, trimers, oligomers, and polymers formed from any monosaccharide units, preferably one or more of the above monosaccharides.

Those analogs of the compounds of Figures IV and V may be phloretin, 4,2,4'-trihydroxychalcone, or the like, or a combination comprising one or more of these compounds.

An extract of *Glycyrrhiza uralensis* or *Glycyrrhiza glabra* may be used as a source of the compounds of Formulae IV and V Methods for synthesizing or isolating Compounds according to Formulae IV and V, its pharmaceutically acceptable salts or esters, and its selectively substituted analogs, are known in the art. See, for example, S. K. Srivastava et al., Indian J. Chem., Sect. B (1981), 20B (4): 347-8; and F. A. Macias et al., Phytochemistry (1998), 50(1): 35-46.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" a neoplasm or cancer, as the term is used herein, encompasses both prevention of the disorder and treatment of the disorder in a clinically symptomatic individual.

The term "pharmaceutically acceptable carrier" includes a material which is not biologically or otherwise undesirable. Much a material may be administered to an individual along with the selected active agent without causing any undesirable biological effects or interacting in a deleterious manner with any of the other components of the pharmaceutical composition in which it is contained.

Certain aspects of the invention will now be exemplified. The experiments detailed below are given by way of example only and are not intended to limit the scope of the invention as defined in the accompanying claims.

EXAMPLES

The present investigation uses two types of cancer cells: A2780 and PTX-10. A2780 is typical of most human ovarian cancers and is not known to be drug-resistant. PTX10 is a taxol-resistant variant of A2780. These two cell types provide a model to compare the effectiveness of the compositions of the present invention against a typical ovarian human cancer where taxol would be a useful treatment and a tumour line where taxol is not useful in treatment.

The experimental conditions common to all three experiments are set forth below:

Cell lines: A2780 and PTX-10 cell lines were from National Institute of Health, Bethesda, Md.

Cell Culture: Both cell lines were cultured in RPMI 1640 supplemented with 10% foetal bovine serum, L-glutamine and antibiotics according to the method of Halicka et al. (Int. J. Oncology 1:437-48, 1997). All media, supplements, and antibiotics were obtained from Life Technologies (Grand Island, N.Y.). The cultures were periodically tested for Mycoplasma infection.

To maintain asynchronous exponential growth, these adherent cells were routinely seeded at $3 \times 10^5$ in a T-75 flask and incubated at 37° C. in 5% $CO_2$ for 5-6 days and then repassaged at a 1:10 dilution by trypsinisation (0.25% trypsin/1 mM EDTA). Morphological changes and cell counts of the control and treated cancer cells were determined by light microscopy. Only exponentially and asynchronously growing cells were used in all experiments.

Inhibition of Cell-Growth and Viability AssASYS: The MTT reagent kit was purchased from Boehringer Mannheim (Roche Diagnosis Corp, Indianapolis, Ind.) to count viable cells. Tetrazolium dye (MTT) is cleaved to form formazan by metabolically active cells and exhibits a strong red absorption band at 550-618 nm. The protocol for the cell viability assay was provided by the manufacturer and modified in our laboratory as described below:

Ovarian cancer cells were seeded in 96 well microtiter plates at a concentration of $6 \times 10^3$ cells per well, in a volume of 100 μL of cell culture medium. After 24 hours, 20 μL aliquots of the compounds at various concentrations were added to the attached cells. Each concentration was plated into 3 wells to obtain mean values. To eliminate any solvent effect, 20 μL of the solvent used in the preparation of the highest concentration of the compounds (a maximum of 0.5% by volume of DMSO) was added to the control cells in each well.

The plates were incubated at 37° C. in the $CO_2$ incubator for 72 hours. At the end of day 3, the culture medium was carefully removed without disturbing the cells, and replaced by 100 μL of fresh cell medium. 10 μL of MTT reagent was added to each well and the plates were incubated again in the $CO_2$ incubator at 37° C. for 4 hours. 100 μL of SDS solubilising reagent (from Boehringer Mannheim) was added to each well. The plate was allowed to stand overnight in the $CO_2$ incubator and read by ELISA Reader (EL800, Bio-Tek Instruments, Inc.) at a wavelength of 570 nm. The percent cell viability was calculated according to the equation below:

100% (absorption of the control cells−absorption of the treated cells)/absorption of the control cells.

By definition, the viability of the control cells, from the untreated cultures, was defined as 100%.

Three different compositions were used to treat the two cell types and the results of those experiments are details below.

Experiment 1

The antiproliferative activity of a compound according to Formula I against two human ovarian cancer cell lines, one sensitive (A2780) and the other resistant (PTX-10) to taxol was studied. The dose-response curves indicate that the A2780 cell line is more sensitive to the compound according to Formula I than PTX-10.

Experiment 2

The antiproliferative activity of a compound according to Formula V against two human ovarian cancer cell lines sensitive (A2780) and resistant (PTX-10) to taxol was explored. The dose-response curves indicate that the PTX-10 cell line is more sensitive to the compound according to Formula V than A2780.

Experiment 3

The antiproliferative activity of a compound according to Formula III against two human ovarian cancer cell lines sensitive (A2780) and resistant (PTX10) to taxol was studied. The dose-response curves indicate that the PTX-10 cell line is slightly more sensitive to the compound according to Formula III than A2780.

Experiment 4

A second set of experiments were carried out showing how the compounds in the formulations of the invention act in synergy with one another. The experimental results differ slightly from those reported above as the experimental work was carried out in a different laboratory and under slightly different conditions. In the second set of experiments the MTT reagent kit was purchased from Sigma-Aldridge in the UK and, due to time constraints; the cells were only incubated overnight prior to being treated with the drugs. The cell lines were also of different origin (the second set being obtained directly from Dr Marianne Poruch of the NIH, Bethesda Md., USA) and may have been subjected to different conditions during storage.

Table 1 shows IC50 in micromoles for the three different drugs when tested in the new system under the conditions in the second set of experiments.

TABLE 1

| Agent | A2780 | PTX10 |
|---|---|---|
| Formula I | 0.81 ± 0.13 | 4.72 ± 3.7 |
| Formula V | 2.4 ± 0.42 | 0.30 ± 0.13 |
| Formula III | 0.67 ± 0.23 | 0.59 ± 0.38 |

Synergy is demonstrated between the compounds as calculated using CalcuSyn 'software for dose effect analysis' Biosoft© 2005.

The combination index method is based on that described by Chou and Talalay and the computer software of Chou and Chou and CalcuSyn™. The ranges of CI and the symbols are refined from those described earlier by Chou. CI<1, =1 and >1 indicate synergism, additive effect and antagonism, respectively.

The tables below show the CI at ED90 for A2780 and PTX-10 cell lines when treated with different combinations of the compounds according to the present invention.

TABLE 2

| Agent | A2780 | PTX10 |
|---|---|---|
| I + V | 1.01 | 0.31 |
| I + III | 0.14 | 0.38 |
| V + III | 1.67 | 0.45 |

TABLE 3

| Range of CI | A2780 PTX10 |
|---|---|
| <0.1 | Very strong synergism |
| 0.1-0.3 | Strong synergism |
| 0.3-0.7 | Synergism |
| 0.7-0.85 | Moderate synergism |
| 0.85-0.90 | Slight synergism |
| 0.90-1.10 | Nearly additive |

When the data presented in table 2 is analysed with respect to the range of combination indices shown in table 3 it can be seen that a score of around 0.3 lies on the cusp of both 'synergism' and 'strong synergism'. The compounds in combination I+V, I+III, and III+V are all strongly synergistically or synergistic when applied together to the PTX-10 cell line indicating that all combinations of the drugs will give synergistic effects on taxol resistant cell lines.

The results show that these combinations of compounds are more effective for the treatment of taxol resistant neoplasias than for the treatment of taxol susceptible cancers. In fact, for some of the combinations the taxol susceptible cancer cell line showed antagonistic rather than synergistic effects.

Much of the work was carried out such that the compounds were present at around 1:1 with respect to the IC50. Results using a 1:1 ratio showed strong synergism and so a preferred composition has those compounds of Formulae I, V and III in ratios of about 1:1:1. During the experimental work it was noted that some other relative ratios of the components were particularly effective. Combinations of compounds of Formulae I, V and III in the ratios 4:4:1 and 9:1:2 are particularly advantageous.

Preferred compositions of the invention have these components present in the particular ratios given above. In methods of treatment the actives are preferably administered to patients in need thereof in the amounts according to these ratios. Components of the composition of the invention may be administered simultaneously at the same time, or sequentially such that the plasma level of the components are in the approximate ratios given above.

Composition Examples

Oral Syrup 25 mg of a Compound of Formula I, 2.5 mg of a compound according to Formula III and 25 mg of a Compound of Formula V were mixed with Citric Acid Monohydrate (105 mg), Sodium Hydroxide (18 mg), spearmint flavouring and made up to 100 mL with distilled water to give a syrup suitable for oral administration.

Injectable Formulation 25 mg of a Compound of Formula I, 2.5 mg of a compound according to Formula III and 25 mg of a Compound of Formula V were mixed with Dextrose Monohydrate q.s. to make isotonic, Citric Acid Monohydrate (10.5 mg) Sodium Hydroxide (1.8 mg) and Water for Injection q.s. to 10.0 mL to give a formulation suitable for injection.

Tablets A 25 mg of a Compound of Formula I, 2.5 mg of a compound according to Formula III and 25 mg of a Compound of Formula V were mixed with lactose (55 mg), corn starch 1(30 mg), microcrystalline cellulose (35 mg) and polyvinylpyrrolidone (PVP) (15 mg). The mixture was screened and worked with further corn starch (60 mg) and water to form a granulate which is dried and screened. Sodium-carboxymethyl starch (23 mg) and magnesium stearate (2 mg) were added and mixed in and the mixture was compressed to form tablets.

Tablets B 25 mg of a Compound of Formula I and 25 mg of a Compound of Formula V were mixed with lactose (52.5 mg), corn starch 1(30 mg), microcrystalline cellulose (35 mg) and polyvinylpyrrolidone (PVP) (15 mg). The mixture was screened and worked with further corn starch (60 mg) and water to form a granulate which is dried and screened. Sodium-carboxymethyl starch (23 mg) and magnesium stearate (2 mg) were added and mixed in and the mixture was compressed to form tablets.

Tablets C 25 mg of a Compound of Formula I and 2.5 mg of a compound according to Formula III were mixed with lactose (40 mg), corn starch 1(20 mg), microcrystalline cellulose (35 mg) and polyvinylpyrrolidone (PVP) (15 mg). The mixture was screened and worked with further corn starch (60 mg) and water to form a granulate which is dried and screened. Sodium-carboxymethyl starch (23 mg) and magnesium stearate (2 mg) were added and mixed in and the mixture was compressed to form tablets.

Additional formulations useful for implant into, for example, a cavity remaining after surgical removal of an ovarian or breast tumour, are also contemplated. The skilled man could manufacture such a formulation from knowledge already available in the art and with no inventive contribution of his own.

Acknowledgments

The inventor and applicant would like to thank Dr Marianne Poruch of the NIH in Maryland for donation of some cell lines used in the experimental section.

The invention claimed is:

1. A method of reducing cell proliferation in an individual having neoplasia, wherein the method consists essentially of administering to the individual synergistically effective combinations, with respect to one another, selected from the group consisting of:

i) a compound having the structure of Formula I;

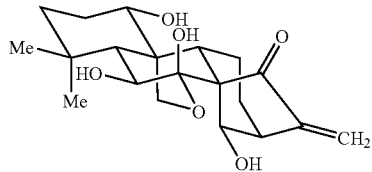

Formula I its pharmaceutically acceptable salts and esters, selectively substituted analogues, or a combination of one or more of the foregoing compounds together with a compound having the structure of Formula II;

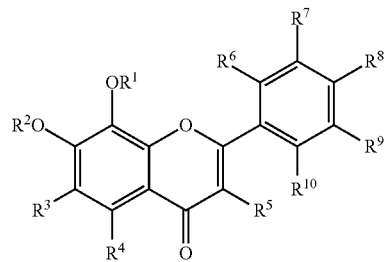

Formula II wherein $R^1$ is hydrogen, $C_1$-$C_6$ alkyl; $R^2$ is hydrogen, $C_1$-$C_6$ alkyl, or $C_2$-$C_6$ acyl; and $R^3$-$R^{10}$ are independently hydrogen, hydroxy, $C_1$-$C_6$ alkyl, $C_1$-$C_6$ alkoxy, or $C_2$-$C_6$ acyl, with the proviso that at least four of $R^3$-$R^{10}$ are hydrogen, its pharmaceutically acceptable salts and esters, selectively substituted analogues, or a combination of one or more of the foregoing compounds;

ii) the compound having the structure of Formula I, its pharmaceutically acceptable salts and esters, selectively substituted analogues, or a combination of one or more of the foregoing compounds and a compound having the structure of Formula IV

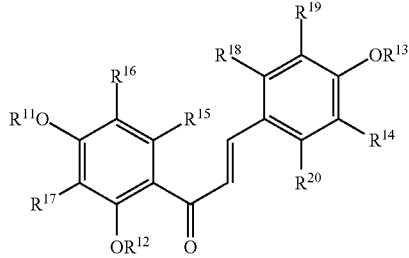

Formula IV wherein $R^{11}$-$R^{13}$ are independently hydrogen or $C_1$-$C_6$ alkyl; and $R^{14}$-$R^{20}$ are independently hydrogen, $C_1$-$C_6$ alkyl, $C_1$-$C_6$ alkoxy, or $C_2$-$C_6$ acyl, with the proviso that at least three of $R^{14}$-$R^{20}$ are hydrogen, its pharmaceutically acceptable salts and esters, selectively substituted analogues, or a combination of one or more of the foregoing compounds; and iii) a compound of Formula II its pharmaceutically acceptable salts and esters, selectively substituted analogues, or a combination of one or more of the foregoing compounds and Formula IV, its pharmaceutically acceptable salts and esters, selectively substituted analogues, or a combination of one or more of the foregoing compounds, and wherein for the combinations ii) and iii) the neoplasia is a chemotherapy resistant neoplasia.

2. The method of claim 1 wherein the neoplasia to be treated is prostate cancer, breast cancer, endometrial cancer, colon cancer, lung cancer, bladder cancer, testicular cancer, ovarian cancer, thyroid cancer or bone cancer.

3. The method of claim 1 wherein the neoplasia to be treated is taxol-resistant ovarian or breast cancer.

4. The method of claim 1 wherein the compound having the structure of Formula II is substituted so that $R^1$ is methyl, $R^2$ is hydrogen, and $R^3$-$R^{10}$ are independently hydrogen, methyl, ethyl, methoxy, ethoxy, acetyl, or propionyl, with the proviso that at least five of $R^3$-$R^{10}$ are hydrogen.

5. The method of claim 4 wherein the compound having the structure of formula II is substituted so that it has the structure of Formula III Formula III

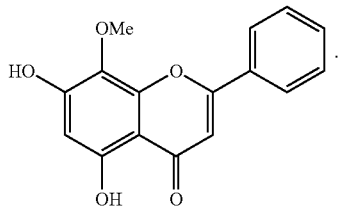

6. The method of claim 1 wherein the compound having the structure of Formula IV is substituted so that $R^{11}$-$R^{13}$ are hydrogen and $R^{14}$-$R^{20}$ are independently hydrogen, methyl, ethyl, methoxy, ethoxy, acetyl, or propionyl, with the proviso that at least four of $R^{14}$-$R^{20}$ are hydrogen.

7. The method of claim 6 wherein the compound having the structure of formula IV is substituted so that it has the structure of Formula V Formula V

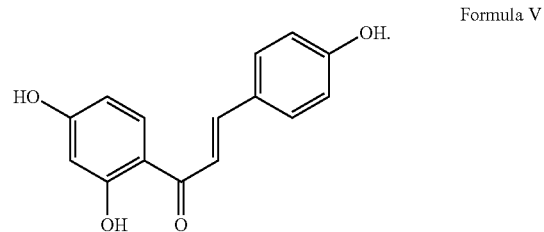 [SMILES: O=C(/C=C/c1ccc(O)cc1)c1ccc(O)cc1O]

8. The method of claim 1 wherein compounds according to Formulae I, II, and IV are obtained from extracts.

9. The method of claim 1, wherein combination iii) is administered, wherein the compound having the structure of formula II is substituted so that it has the structure of Formula III, and wherein the compound having the structure of formula IV is substituted so that it has the structure of Formula V.

\* \* \* \* \*